US011337656B1

(12) United States Patent
Saliga et al.

(10) Patent No.: US 11,337,656 B1
(45) Date of Patent: *May 24, 2022

(54) METHOD AND SYSTEM FOR ACQUIRING BIOSIGNALS IN THE PRESENCE OF HF INTERFERENCE

(71) Applicant: NeuroWave Systems Inc., Cleveland Heights, OH (US)

(72) Inventors: Thomas V Saliga, Odessa, FL (US); Stéphane Bibian, Cleveland Heights, OH (US); Tatjana Zikov, Cleveland Heights, OH (US)

(73) Assignee: NeuroWave Systems Inc., Cleveland, OH (US)

(*) Notice: Subject to any disclaimer, the term of this patent is extended or adjusted under 35 U.S.C. 154(b) by 385 days.

This patent is subject to a terminal disclaimer.

(21) Appl. No.: 16/455,903

(22) Filed: Jun. 28, 2019

Related U.S. Application Data

(63) Continuation of application No. 15/233,200, filed on Aug. 10, 2016, now Pat. No. 10,376,220, which is a continuation of application No. 14/687,159, filed on Apr. 15, 2015, now Pat. No. 9,439,601, which is a continuation of application No. 13/335,256, filed on Dec. 22, 2011, now Pat. No. 9,037,225, which is a
(Continued)

(51) Int. Cl.
*A61B 5/00* (2006.01)
*A61B 5/30* (2021.01)
*A61B 5/369* (2021.01)
*A61B 5/389* (2021.01)
*A61B 5/398* (2021.01)

(52) U.S. Cl.
CPC .......... *A61B 5/7217* (2013.01); *A61B 5/30* (2021.01); *A61B 5/369* (2021.01); *A61B 5/389* (2021.01); *A61B 5/398* (2021.01); *A61B 5/4839* (2013.01); *A61B 5/725* (2013.01)

(58) Field of Classification Search
None
See application file for complete search history.

(56) References Cited

U.S. PATENT DOCUMENTS 4,583,190 A * 4/1986 Salb ............... A61B 5/374
708/404
6,256,531 B1 * 7/2001 Ilmoniemi ........ A61B 5/245
600/544
(Continued)

*Primary Examiner* — Etsub D Berhanu
(74) *Attorney, Agent, or Firm* — Brian Kolkowski

(57) ABSTRACT

The present invention, herein is a method and apparatus that significantly limits the effect of high frequency ("HF") interferences on acquired electro-physiological signals, such as the EEG and EMG. Preferably, this method comprises of two separate electronic circuitries and steps or electronics for processing the signals. One circuit is used to block the transmission of HF interferences to the instrumentation amplifiers. It is comprised of a front-end active filter, a low frequency electromagnetic interference ("EMI") shield, and an isolation barrier interface which isolates the patient from earth ground. The second circuit is used to measure the difference in potential between the two isolated sides of the isolation barrier. This so-called "cross-barrier" voltage is directly representative of the interference level that the instrumentation amplifier is subjected to. This circuit is used to confirm that the acquired signals are not corrupted by the interference.

20 Claims, 13 Drawing Sheets

Related U.S. Application Data continuation of application No. 11/827,906, filed on Jul. 13, 2007, now Pat. No. 8,108,039.

(56) References Cited

U.S. PATENT DOCUMENTS

| | | | |
|---|---|---|---|
| 6,430,437 B1* | 8/2002 | Marro | A61B 5/0002 600/544 |
| 2002/0173729 A1* | 11/2002 | Viertio-Oja | A61B 5/374 600/544 |

* cited by examiner

METHOD AND SYSTEM FOR ACQUIRING BIOSIGNALS IN THE PRESENCE OF HF INTERFERENCE

CROSS REFERENCE TO RELATED APPLICATIONS

This application is a continuation of U.S. patent application Ser. No. 15/233,200, which was filed on Aug. 10, 2016 and which is a continuation of U.S. patent application Ser. No. 14/687,159, which was filed on Apr. 15, 2015 and issued as U.S. Pat. No. 9,439,601 on Sep. 13, 2016, and which is a continuation of U.S. patent application Ser. No. 13/335,256 which was filed on Dec. 22, 2011 and issued as U.S. Pat. No. 9,037,225 on May 19, 2015, and which is a continuation of U.S. patent application Ser. No. 11/827,906 which was filed on Jul. 13, 2007 and issued as U.S. Pat. No. 8,108,039 on Jan. 31, 2012.

BACKGROUND OF THE INVENTION

Field of the Invention

This invention relates to the monitoring of electro-physiological signals of a subject in a harsh electrical environment. This invention further relates to the monitoring of EEG signals of a patient, while said patient is being operated on with an electrical surgical knife.

BRIEF DESCRIPTION

Disclosed, herein, is a method and apparatus that significantly limits the effect of high frequency ("HF") interferences on acquired electro-physiological signals, such as the EEG and EMG. This method comprises of two separate electronic circuitries and processing means. One circuitry is used to block the transmission of HF interferences to the instrumentation amplifiers. It is comprised of a front-end active filter, a low frequency electromagnetic interference ("EMI") shield, and an isolation barrier interface which isolates the patient from earth ground. The second circuitry is used to measure the difference in potential between the two isolated sides of the isolation barrier. This so-called "cross-barrier" voltage is directly representative of the interference level that the instrumentation amplifier is subjected to. This circuitry is used to confirm that the acquired signals are not corrupted by the interference. The processing means further use both the acquired electro-physiological signals and the cross-barrier voltage measurement to qualitatively or quantitatively assess the state or well-being of the patient.

TECHNICAL REVIEW

Clinical environments can be particularly hostile for systems dedicated to real-time acquisition of electro-physiological signals. Surgical equipment, such as electro-surgical units ("ESU"), are a typical source of high frequency (HF) interferences (>100 kHz). Electrodes used to measure bio-potentials can be subject to common mode noise whose amplitude can reach several orders of magnitudes higher than the range the bio-signals such as ECG, EOG, EEG, EMG and the like, which need to be acquired. A slight difference between the noise at the recording electrode site and the noise at the reference electrode site usually induces the saturation of the instrumentation amplifier. In this case, the acquired signal cannot be salvaged, as it does not contain any viable information.

Critical applications that rely on electro-physiological data acquisition to continuously monitor the patient's state will therefore suffer from HF interferences. If the source signal is lost due to these interferences, these monitoring systems will not be able to output reliable information pertinent to the patient state. In systems where this information is used to provide or adjust a treatment, the loss of the source signal is cause for concern.

In the past, a number of researchers have disclosed methods, which attempt to alleviate HF interference in high gain instrumentation amplifiers. For example, in U.S. Pat. No. 4,537,200 to Windrow the method involves both passive and active input HF filters followed by proper isolation, and a hard-wired adaptive filter to remove the interference based on a reference electrode that provides a regressive channel used by the adaptive filter. U.S. Pat. No. 6,430,437 to Marro uses a combination of a passive and active input filters, a low isolation interface to minimize the leakage capacitance, and a low frequency shielding. U.S. Pat. No. 6,985,833 to Shambroom proposes the use of a hard-wired quantal (i.e., on/off) detection of the presence of ESU. When ESU is detected, a logic flag is raised. The computing means then rejects the current epoch and replaces it with the previously good epoch.

These three references are attempts to develop biopotential data acquisition systems that are capable of working in a harsh HF electrical environment. Unfortunately none are capable of actually measuring residue interferences that get through the front end filters. In the current state of the art this is absolutely critical if one requires real time monitoring. While Shambroom has proposed a circuitry that can detect the presence of ESU, then reject the corrupted epochs and finally replace the rejected epochs with previous epochs. This does not allow for the actual measuring of biopotentials while an ESU is in use.

Conversely Widrow and Marro have taken a different approach, and have attempted to filter out all interferences. This works well as long as the interferences are completely filtered out. Unfortunately, often in practice the use of an ESU will cause interference that is too great to be completely eliminated from the signal. In these cases, the acquired biosignals are still be corrupted, albeit with a corrupting noise that is now in the same order of magnitude as the desired signal itself. Therefore, it becomes very difficult to determine that the acquired biosignals are corrupted, and thus cannot be used. Thus the practicality of these systems is questionable in harsh RF environment.

In the presence of HF interferences, the previously mentioned technology either leaves the user with the explicit knowledge that the signals are corrupted, or leaves the user with signals whose integrity cannot be guaranteed. Therefore a need exists for a biosignal data acquisition system that can both filter out large HF interference, and measure the residual interferences to eventually correct them using digital signal processing means. This allows for accurate and reliable data to be acquired while in a harsh HF environment. It is an object of the present invention to provide a robust system that meets such a need.

The present invention differs in that a combination of active filters, isolation, shield, measurement circuitry, and software are used to deal with HF interferences. The present invention uses a first line of defense that is optimized using front-end hardware, which dramatically reduces the magnitude of the interference, as seen by the instrumentation amplifiers. The front-end hardware includes: an optimized active front-end HF filter that buffers the instrumentation amplifiers against HF interferences, a high isolation-barrier interface between the patient-side electronics and the computer-side electronics, and a low voltage shield.

As compared to Marro '437 and Widrow '200, this circuitry uses only one active filter at the front-end. The choice of an active filter vs. the passive HF filter architecture proposed by Marro '437 and Widrow '200 is dictated by the need for a high input impedance (>100 MΩ) in the instrumentation amplifier bandwidth, a requirement set forth by the International Federation of Clinical Neurophysiology (IFCN), as a pre-requisite for EEG and EMG data acquisition.

The role of the isolation barrier is two-fold: to provide the necessary patient/earth isolation required by the IEC 60601 standard for medical device safety, and to provide a difficult return-to-earth path for the HF interferences. Marro '437 attempted to achieved this by using opto-isolators to transmit the acquired data from the patient-side electronics to the computer-side electronics. Marro '437 mentions that only opto-isolators are suitable for this application, as they provide an ultra-low coupling capacitance between the patient-side and computer-side ground planes. The Applicants, however, found out unexpectedly that individual drum inductor coils loosely coupled end-to-end across the isolation barrier implements a pulse transformer to provide galvanic isolation can also be used effectively.

In many cases, the optimized front-end will block almost all of the HF interference. In many cases, the remaining HF noise that still perturbs the input of the instrumentation amplifier, is significantly less than the signal of interest, in which case the acquired data will only be marginally corrupted by the interference. In other cases, however, the HF interferences are so large or close to the recording electrode sites that the residual interference noise level is about the same order of magnitude as the signal of interest. The acquired signal is therefore corrupted by a wide-band noise, which will perturb any subsequent analysis and patient state determination. It is therefore necessary to properly detect such situations in order to take appropriate action.

Detecting wide-band noise in acquired data can be particularly difficult when the signals of interest are already wide-band noise-like signals, such as EEG and EMG signals. Systems equipped with only the front-end electronics, as described above, are practical only when HF interference are always completely blocked. Since this is not the case in practice, the present invention preferably uses the addition of a secondary circuitry whose role is to measure the difference in potential between the isolated patient-side electronics and the computer-side electronics. This circuitry provides a cross-barrier voltage measurement that represents the magnitude of the corrupting interference. In electrically quiet environments (no HF interference), or when the HF interference are small enough to be significantly attenuated by the first circuitry, this voltage will be low, close to 0. If the HF interference is large enough that it cannot be completely rejected, the measured cross-barrier voltage will be higher, thereby indicating that the acquired data may be corrupted.

In critical applications, such as patient monitoring, the present invention preferably uses a post-processing algorithm may opt for rejecting the acquired samples for which the cross-barrier voltage was high. In other embodiments, special techniques may be used to extract the signal of interest from the acquired data see for instance *A wavelet based de-noising technique for ocular artifact correction of the electroencephalogram*. Zikov, et al. Eng. in Med. and Bio. $24^{th}$ Ann. Conf. p 98-105 vol. 1 (2002).

A device detecting the presence of HF noise was proposed by Shambroom '833. However, the described circuitry only documents the presence or absence of RF noise. In contrast, the present invention preferably measures the interference which corrupts the instrumentation amplifier. This information can be used dynamically by the processing means to assess the best course of action. Shambroom '833 proposes that corrupted samples be replaced by non-corrupted samples acquired previously. In contrast, the current invention proposes to filter the acquired EEG if the cross-barrier voltage is low enough, and reject completely the corrupted samples if the cross-barrier voltage is too large. The thresholds used to determine whether a sample must be kept, filtered, or rejected can be dynamically changed depending on the sensitivity to HF noise of the processing algorithms.

SUMMARY OF THE INVENTION

The present invention involves the step of using at least one sensor to measure a subject's biopotential signals, in particular EEG or brainwave signals, over a period of time. The biopotential signals can be obtained by any method known in the art, or subsequently developed by those skilled in the art to detect these types of signals. Sensors include but are not limited to electrodes or magnetic sensors. Since brain wave signals are, in general, electrical currents which produce associated magnetic fields, the present invention further anticipates methods of sensing those magnetic fields to acquire brain wave signals similar to those which can be obtained through for example an electrode applied to the subject's scalp. The subject(s) or patient(s) referred to in the present invention can be any form of animal. Preferably the subject(s) are mammal, and most preferably human.

If electrodes are used to pick up the brain wave signals, these electrodes may be placed at one or several locations on the subject(s)' scalp or body. The electrode(s) can be placed at various locations on the subject(s)' scalp in order to detect EEG or brain wave signals. Common locations for the electrodes include frontal (F), parietal (P), anterior (A), central (C) and occipital (O). In order to obtain a good EEG or brain wave signal it is desirable to have low input impedances for the electrodes. Typical EEG electrode connections may have an impedance in the range of 5 to 30 kΩ. A conductive paste or gel may be applied to the electrode to create a connection with an impedance below 2 kΩ. Alternatively, the subject(s) skin may be mechanically abraded, the electrode may be amplified or a dry electrode may be used. Dry physiological recording electrodes of the type described in U.S. Pat. No. 6,782,283 which is hereby incorporated by reference. Dry electrodes provide the advantage that there is no gel to dry out, no skin to abrade or clean, and that the electrode can be applied in hairy areas such as the scalp. Additionally if electrodes are used as the sensor(s), preferably at least two electrodes are used, one signal electrode and one reference electrode.

The electrodes can be connected to the front end circuitry by means of electrical leads. These leads can be of any type known in the art, but preferably the leads are shielded. The use of shielded leads adds additional protection from electrical interference. Preferably the leads include a typical female snap connector for attachment to the electrodes at one end and some other suitable connector for attachment to the front end circuitry at the other end.

The present invention uses specifically designed front end circuitry to reduce and filter HF interference. A great variety of filters could be used in the present invention, but preferably they are active filters due to the need for high input impedance. The active filter is preferably a Sallen Key filter or a modified version of Sallen Key filter. Although, the present invention may also use passive filters such as band pass filters, high pass filters, low pass filters or the like or any combination thereof to obtain the needed filtering characteristics. Additionally, the front end filters could be either single pole types or multi-pole types.

An isolation barrier is used to electrically separate the patient-side electronics from the computer-side electronics. The isolation barrier can use opto-isolators, transformers, electrostatically screened transformers, data coils or the like to isolate the two sets of electronics. But preferably the isolation barrier comprises of individual drum inductor coils loosely coupled end-to-end across the isolation barrier for data transfer. Additionally, a preferred embodiment of the present invention includes a thick dielectric barrier within the isolation barrier to better isolate the patient-side electronics from the computer-side electronics. This barrier could be made out of any appropriate dielectric material known in the art, but preferably is dimensioned to provide a low capacitive coupling between the two electronics, and EMI rejection for radiated emissions of 80 MHz and higher. Preferably the barrier is made of a dielectric plastic.

A unique circuitry which is detailed herein is used at the isolation barrier interfaces to measures the cross-barrier voltage between the patient-side and computer-side electronics, and relay that information to a processor. The data is then sent for display or outputted for further analysis.

The cross-barrier voltage measurement is representative of the magnitude of the HF interference. In electrically quiet environments (no HF interference), or when HF interference are small enough that they can be significantly attenuated by the first circuitry, this voltage will be low, close to 0. If the HF interference is too large to be completely rejected by the first circuitry, the measured cross-barrier voltage will be higher, thereby indicating that the acquired data may be corrupted. In critical applications, such as depth of anesthesia monitoring, the post-processing algorithm may opt for rejecting the acquired samples for which the cross-barrier voltage was high. In other embodiments, special techniques may be used to extract the signal of interest from the acquired data, see *A wavelet based de-noising technique for ocular artifact correction of the electroencephalogram.* Zikov, et al. Eng. in Med. and Bio. 24$^{th}$ Ann. Conf. p 98-105 vol. 1 (2002), which is herein incorporated by reference.

Earlier attempts have left the end user either with the explicit knowledge that the signals are corrupted, or leaves the user with signals whose integrity cannot be guaranteed, especially if an electrosurgical unit ("ESU") is in operation. Therefore the present invention provides a biopotential data acquisition system that can filter out interference, measure the level of HF interference, and eventually correct for any residual interference that may corrupt the acquired signals. This allows for the acquisition of accurate and reliable data, while in a harsh HF electrical environment.

The invention therefore provides a significant advantage in the area of anesthesia management during surgery with an ESU, since the accuracy and reliability of the real-time monitoring systems are desired in order for the anesthesiologist to properly maintain a desired level of anesthesia throughout the surgery. Without the present invention, the user of a data acquisition system during ESU operation either cannot be certain that the acquired signals are representative of the true electro-physiological state of the patient, or the user is left without any viable signals as long as the ESU is in operation. This could lead to the administration of improper doses of anesthetic, which could lead to patient awareness during surgery, or drug overdose, which both lead to undesirable outcomes.

In one embodiment the invention is a method of acquiring signals from a subject in the presence of HF interference comprising the steps of attaching at least 2 electrodes to a subject, acquiring signals from the subject using an amplification circuitry for HF rejection, with said circuitry comprising at least one active input filter, a multistage amplification circuitry, an optimized low frequency shield, an isolation barrier where power is transmitted via an optimized transformer, and data is transmitted via at least one data coil; then measuring the level of remaining HF interference across said isolation barrier, and transmitting the signals and measured HF level to a processor.

In another embodiment the invention is a method to monitor brain waves of a subject, comprising the steps of attaching at least 2 electrodes on said subject; acquiring signals using an amplification circuitry comprising at least one active input filter, a multistage amplification circuitry, an optimized low frequency shield, an isolation barrier where power is transmitted via an optimized transformer, and data is transmitted via at least one data coil, a processor, a display; then measuring the level of HF interference across the isolation barrier, processing said acquired signals, outputting results.

In yet another embodiment the invention is a method of monitoring brain waves of a subject in a harsh HF environment, comprising the steps of attaching at least 2 electrodes on said subject; acquiring signals using an amplification circuitry for HF rejection, said circuitry comprising at least one active input filter, a multistage amplification circuitry, an optimized low frequency shield, an isolation barrier where power is transmitted via an optimized transformer, and data are transmitted via at least one data coil, a processor, a display; then measuring the level of remaining HF interference across the isolation barrier processing the acquired signals outputting results.

In still yet another embodiment the in invention is a method of monitoring brain waves of a subject in a HF environment, comprising the steps of attaching at least 2 electrodes on said subject; acquiring signals using an amplification circuitry for HF rejection, with said circuitry comprising at least one active input filter, a multistage amplification circuitry, an optimized low frequency shield, an isolation barrier where power is transmitted via an optimized transformer, and data are transmitted via at least one data coil, a processor, a display; then measuring the level of remaining HF interference across the isolation barrier, detecting the presence of corrupting HF interference, processing said acquired signals, outputting results.

In but another embodiment the in invention is a method of acquiring continuous brain wave signals from a subject in the presence of RF interference, for use in closed-loop control anesthesia delivery, with said method comprising the steps of attaching at least 2 electrodes on said subject; collecting signals using an amplification circuitry for HF rejection, said circuitry comprising at least one active input filter, a multistage amplification circuitry, an optimized low frequency shield, an isolation barrier where power is transmitted via an optimized transformer, and data are transmitted via at least one data coil; then measuring the level of remaining HF interference across said isolation barrier; and transmitting the signals and measured HF level to a processor.

In still but another embodiment the in invention is a method of monitoring continuous brain wave signals from a subject in the presence of RF interference, for use in closed-loop control in anesthesia or sedation drug delivery, with said method comprising the steps of attaching at least 2 electrodes on said subject; acquiring signals using an amplification circuitry for HF rejection, with said circuitry comprising at least one active input filter, a multistage amplification circuitry, an optimized low frequency shield, an isolation barrier where power is transmitted via an optimized transformer, and data are transmitted via at least one data coil; then measuring the level of remaining HF interference across the isolation barrier, transmitting the signals and measured HF level to a processor, detecting the presence of corrupting interference, processing transmitted signals in real-time, outputting results.

In another further embodiment the in invention is a method of quantifying depth of anesthesia and/or depth of sedation of a subject in the presence of RF interference, with said method comprising the steps of attaching at least 2 electrodes on said subject, acquiring signals using an amplification circuitry for HF rejection, with said circuitry comprising at least one active input filter, a multistage amplification circuitry, an optimized low frequency shield, an isolation barrier where power is transmitted via an optimized transformer, and data is transmitted via at least one data coil; then measuring the level of remaining HF interference across the isolation barrier, transmitting the signals and measured HF level to a processor, detecting the presence of corrupting interference, processing the transmitted signals, outputting results.

In still another further embodiment the in invention is a method of acquiring signals from a subject in the presence of electrical interference comprising the steps of attaching at least 2 electrodes to a subject, acquiring signals from the subject using circuitry for rejection of electrical interference, with said circuitry comprising at least one input filter, and an isolation barrier where data is transmitted; measuring the level of remaining electrical interference across said isolation barrier, and transmitting the signals and measured interference level to a processor.

In another proposed embodiment the in invention is a method of acquiring signals from a subject in the presence of electrical interference comprising the steps of attaching at least 2 electrodes to a subject, acquiring signals from the subject using circuitry for rejection of electrical interference, with said circuitry comprising at least one input filter, and a magnetic flux isolation barrier where data is transmitted; transmitting the signals to a processor.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

DETAILED DESCRIPTION

Figure 1:
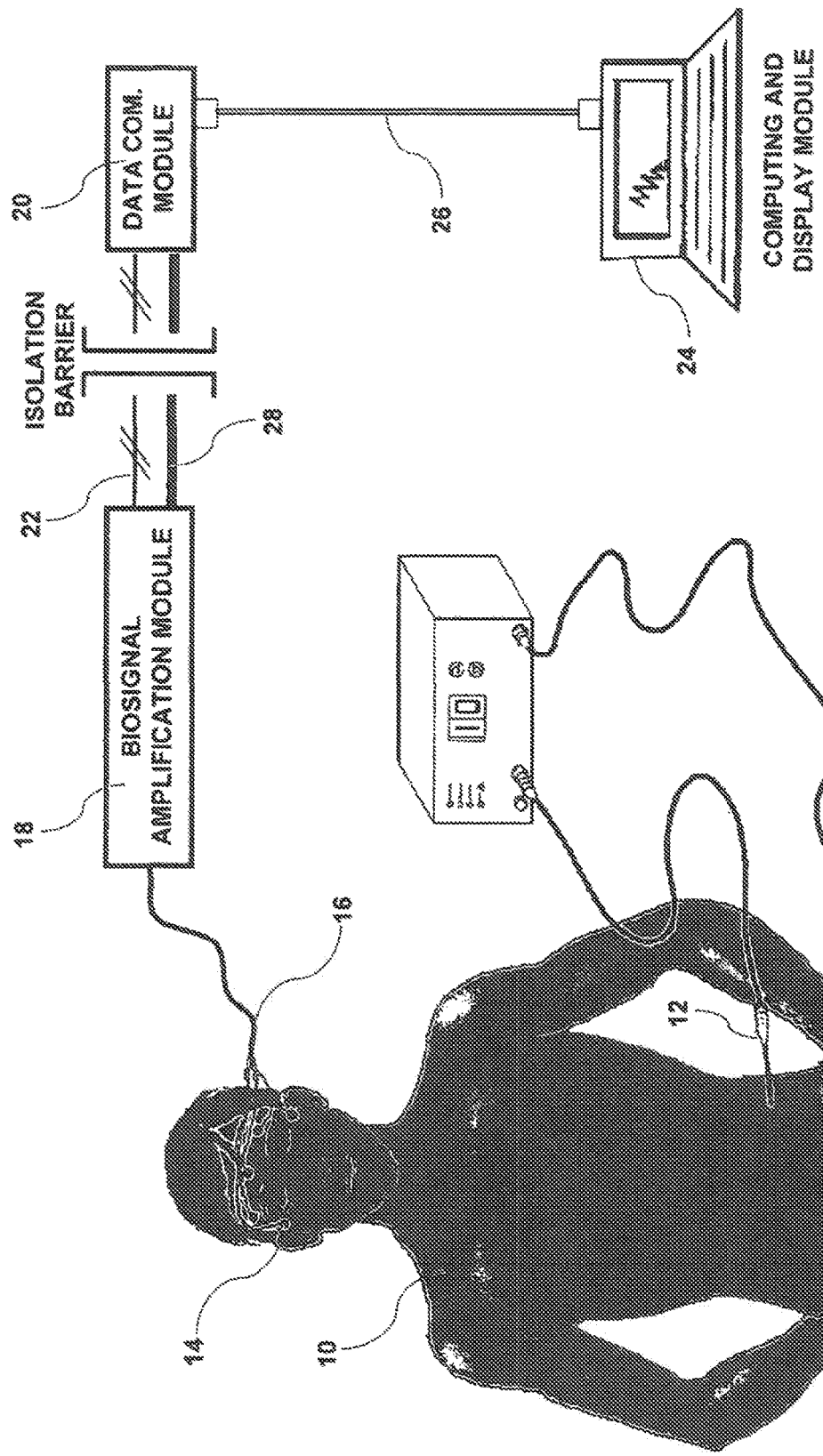
FIG. 1 shows, in diagrammatic form, use of apparatus embodying the invention.

FIG. 1 shows a schematic of the overall system in use while a subject 10 is operated on with an Electro-Surgical Unit (ESU) knife 12. Electrodes 14 are connected to the subject 10. The electrode leads 16 are also connected to the Biosignal Amplification Module (BAM) 18. The digitized data is then sent to a Data Communication Module (DCM) 20 via an isolated bidirectional data link 22. The data link 22 used in this particular embodiment is an isolated electrical link, but a wireless connection, optical connection or the like could also be used with minor modifications to the system. The data link 22 is also used to modify the operating mode of the BAM instrumentation amplifiers using a command message sent by the DCM 20. The BAM 18 receives its power either via the DCM 20 through an isolated electrical power line 28, or through a battery pack.

The DCM 20 collects the digitized biosignals, as well as information about the state of the BAM instrumentation amplifiers and the level of HF interference. The data is organized into a data stream, which is transferred to a Computing and Display Module (CDM) 24 through a data link 26. Likewise this data link 26 may also be wirelessly or optically connected. Power to the DCM 20 can be provided either through a battery pack, or by the CDM 24 using the physical electrical connection between the two modules.

The BAM 18 amplifies, and digitizes a number of biosignals from the subject. These signals can be used by clinical personnel for evaluating the patient's state and well-being, which is done either directly by simple inspection of the displayed waveforms, or indirectly by processing the acquired biosignals and displaying the results of the processed signals.

In the embodiment of FIG. 1, the CDM 24 is used both for processing and display. In other embodiments, the processing can be done at the level of the BAM, DCM, CDM or combination thereof. In yet another embodiment, all processing can be done at the level of the BAM, DCM, or both. In this case, the CDM is used uniquely as a display and user interface.

Figure 2:
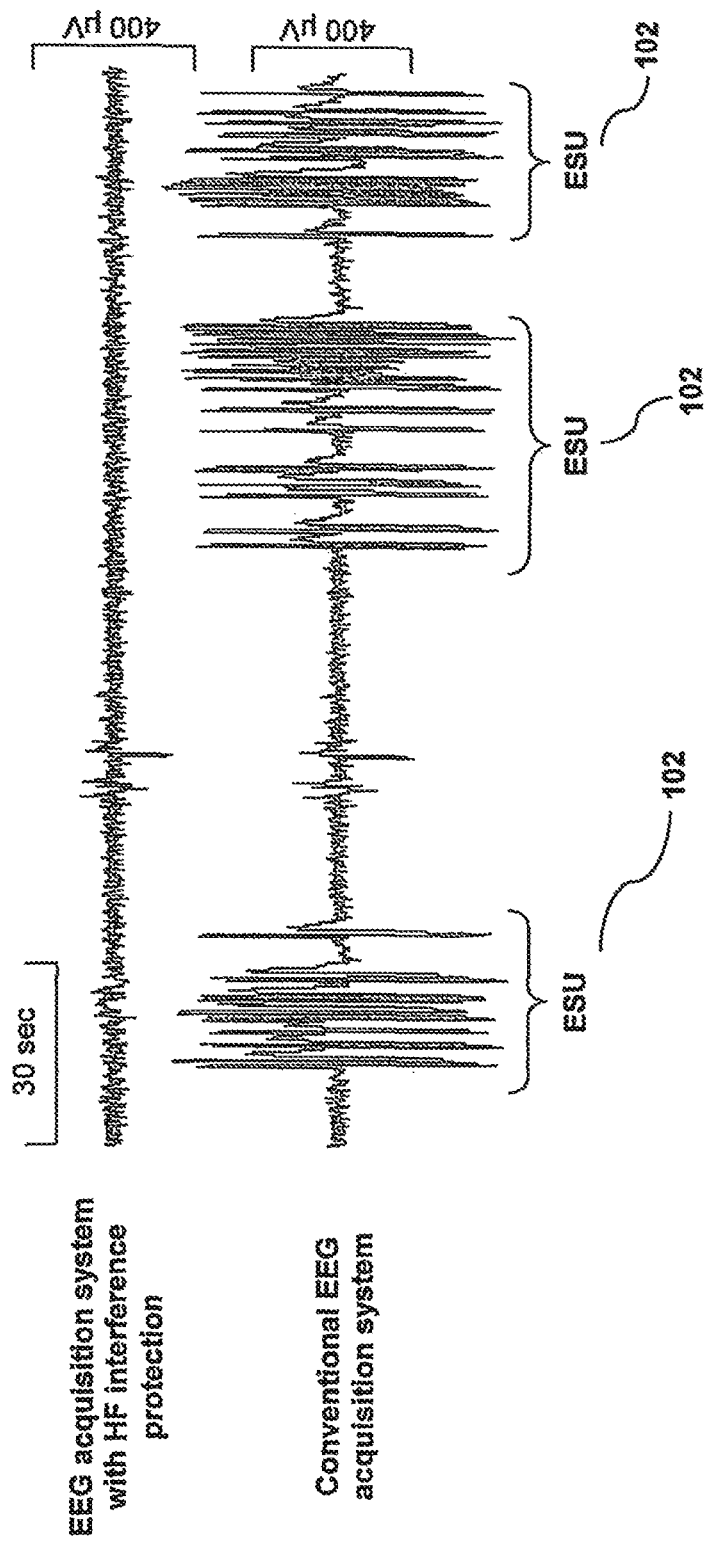
FIG. 2 shows an example chart of ESU rejection in clinical EEG recordings.

High frequency (HF) interferences, such as those produced by ESUs, affect the instrumentation amplifiers in such a way that the amplifiers saturate, resulting in an irremediable loss of the acquired data. FIG. 2 shows an EEG recording obtained using a traditional EEG amplifier, and while a surgeon performed a skin incision using an ESU device. During the incision, the amplifiers are saturated by ESU interference 102 and the EEG signal is lost. Using our proposed system architecture, the HF interference is filtered out before it can saturate the amplification device. The output of the front-end amplifier is thus a signal which contains both the biosignal and the remaining unfiltered HF interference. Since the bandwidth of the biosignal is usually located in the low and very low frequency ranges, post-amplification and anti-aliasing filters strongly attenuate the HF content of the amplified signal, thereby eliminating the remaining HF interference.

Figure 3:
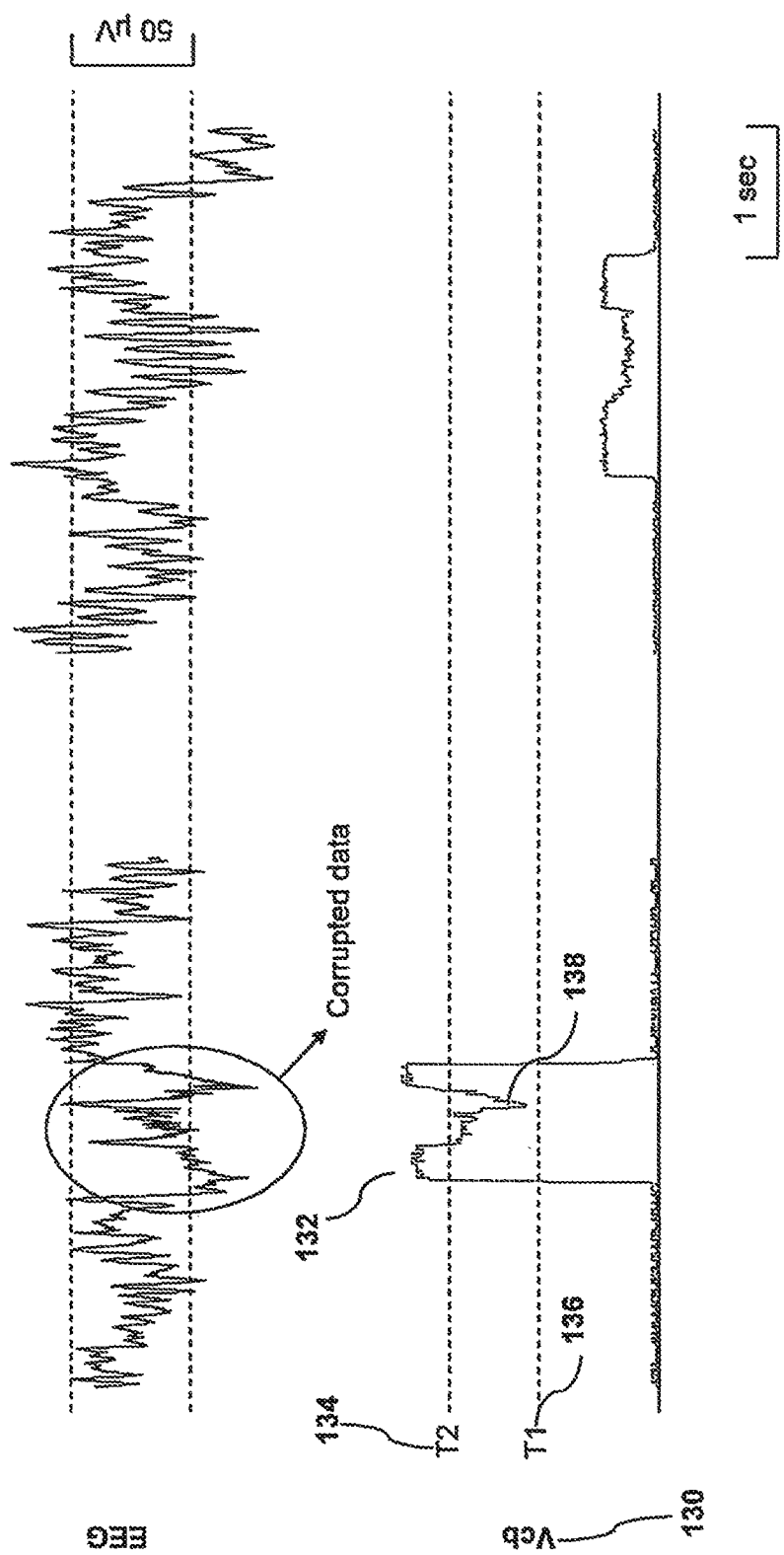
FIG. 3 shows an example chart of clinical EEG recordings with complete and incomplete ESU rejection, and the associated cross-barrier voltage Vcb.

Referring now to FIG. 3, in some cases the level of HF interference is too high. This can happen when the setting of the ESU is high enough, or if the surgical site happens to be in close proximity to the recording electrodes. In these cases, some HF noise may remain, even after the post-amplification filters. This noise will corrupt the acquired biosignal data. Since the noise-to-signal ratio is small in practice, it can be particularly difficult to detect by use of signal processing means alone, and in most cases continuously screening the acquired data to detect such problems is impractical. A solution to alleviate this problem is to use a cross-barrier voltage measurement 130 as a means to quantify the level of HF interference. From this it can be determined how to best treat the data. For instance, if the cross-barrier voltage 132 is too high, e.g., above a certain threshold T2 134, the system may elect to reject the EEG data altogether. Conversely, if the cross-barrier voltage is low enough, e.g., less than a certain threshold T1 136, the EEG data is not significantly perturbed, and may be of good enough quality to allow for post-processing. If the cross-barrier voltage is in between these two thresholds 138, some additional filtering or denoising may be required before using the data. These thresholds can be determined empirically depending on the sensitivity of the application to HF artifacts. These thresholds may remain fixed or may be adapted continuously. Finally, the cross-barrier voltage measurement may be itself processed to extract a trend or calculate an index representing its variation over time, and which can be used to further assess the impact of the HF interference onto the biosignal.

Figure 4:
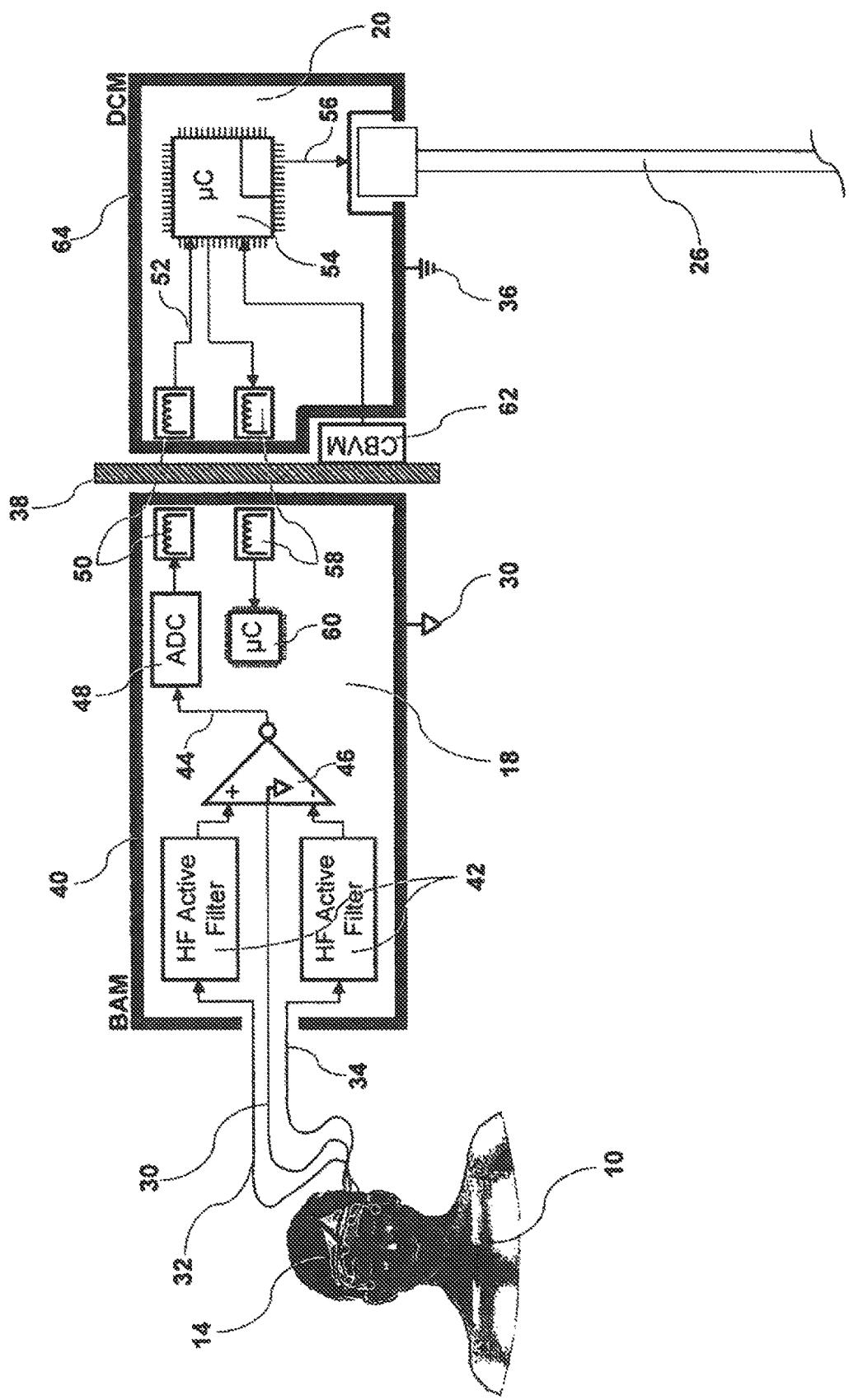
FIG. 4 shows, in diagrammatic form, an overview of the acquisition system schematics.

FIG. 4 is a schematic drawing showing one particular form of the preferred embodiment of the system, which is comprised of two distinct electronics subsystems. The first subsystem is the Biosignal Amplification Module (BAM) 18, which is connected directly to the subject via a ground electrode 30, and at least one measurement electrode 34, or preferably one reference 32 and one measurement electrode 34 per channel; and the second subsystem is the Data Communication Module (DCM) 20, whose ground 36 is connected to the earth ground. Each electronic subsystem is electrically isolated from each others, as per current medical standards (ref. IEC 60601-1) using a properly dimensioned isolation barrier 38 made of a dielectric material. The design of the isolation barrier should be such that EMI immunity is respected, as per the IEC 60601-1-2 standard.

A number of electrodes 14 are attached to the subject. The electrodes can be of any type acceptable for EEG and/or EOG use, including but not limited to gel electrodes, dry electrodes or wet/dry electrodes. The ground electrode lead is connected to the ground 30 of the BAM 18 electronics circuitry, and connected to the chassis and shield 40 of the BAM subsystem. The other non-ground electrodes 32, 34 are connected to independent HF active filters 42, the design of which will be elaborated on later. The output signal 44 of the operational amplifier 46 is then digitized by analog-to-digital converter(s) (ADC) 48. The digital data is then transferred across the isolation barrier 38 from the BAM 18 to the DCM 20 by means of data coils 50. The transmitted digital data 52 is then sent to a microprocessor 54 for initial processing. A bidirectional data bus 56 and data link 26 are then used to transfer the digital data to the CDM 24 for display purposes or further processing. A secondary set of data coils 58 are used to send commands from the DCM 20 to the BAM 18. These commands are processed by the BAM micro-controller 60 in order to change the operating mode of the instrumentation amplifier. A change of operating mode can be initiated automatically for calibration or self-test procedures, or initiated manually by the user via the user interface of the CDM (not shown).

The isolation barrier contains the Cross-Barrier Voltage Measurement (CBVM) electronic circuitry 62, which is used for measuring the level of HF interference. The cross-barrier voltage is a quantitative measure of the potential difference between the DCM 20 and BAM 18 grounds. It is used in post-processing to determine whether the HF interferences were of a low enough level to be successfully rejected by the front-end HF active filters. The cross barrier voltage is sampled and appended to the digital biosignal samples acquired by the BAM 18.

It is important to note that both the BAM 18 and DCM 20 are encased by separate low frequency shields 40 and 64, respectively. The thickness of the shields is calculated to prevent environmental HF interferences from permeating through the shield. Without adequate shielding, environmental HF interferences can disrupt the nominal operation of the system. Details on the design of the shield are discussed below.

Figure 5:
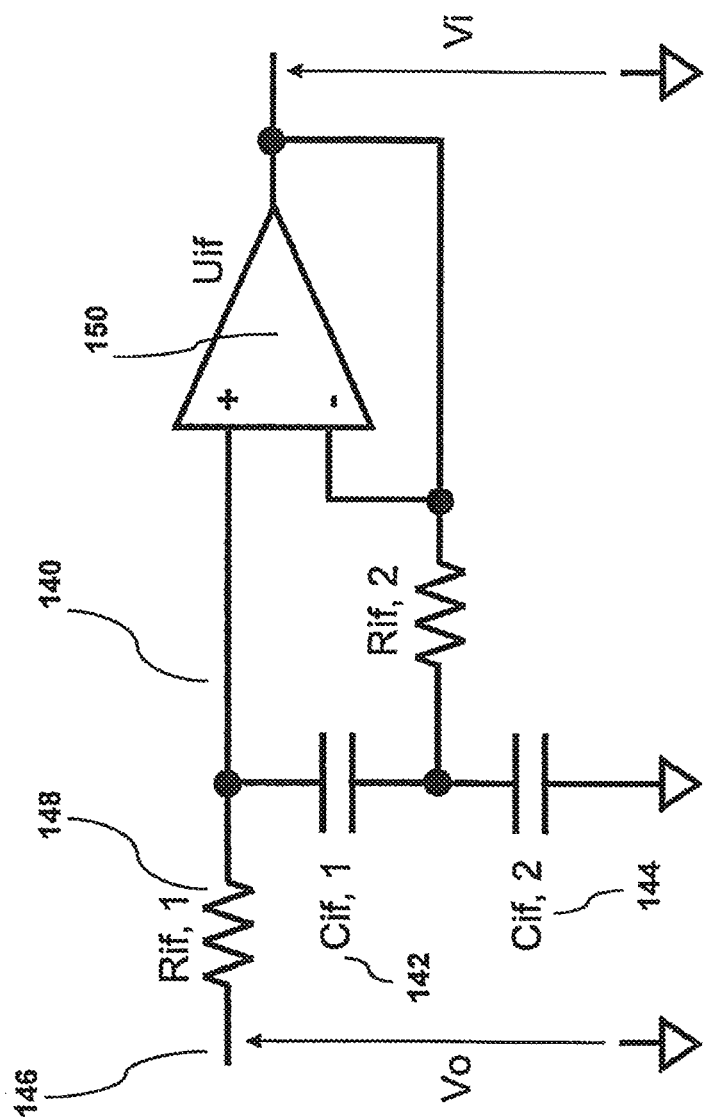
FIG. 5 shows, in diagrammatic form the active filter architecture.

FIG. 5 is a schematic drawing showing one particular form of the preferred embodiment of the active filters 140 used in the system's front-end. The active filter 140 possesses circuit values that allow for the rejection of HF interference while passing signals in the biosignal bandwidth, with little adverse impact on CMRR or input impedance.

At very high frequencies the capacitors (Cif1, Cif2) 142, 144 short-circuit the input signal 146 through the resistor (Rif1) 148 to common. Therefore, the operational amplifier (Uif) 150 does not have a response for the higher frequencies associated with ESU interference. Yet, at lower frequencies the unity-gain feedback signal suffers very little attenuation at the node of Rif1-Cif1-Cif2. Thus, Cif1 142 does not appear to be present since the voltage differential is very small. With Cif1 142 "absent", the input is basically set by the native input impedance of the operational amplifier Uif 150.

Figure 6:
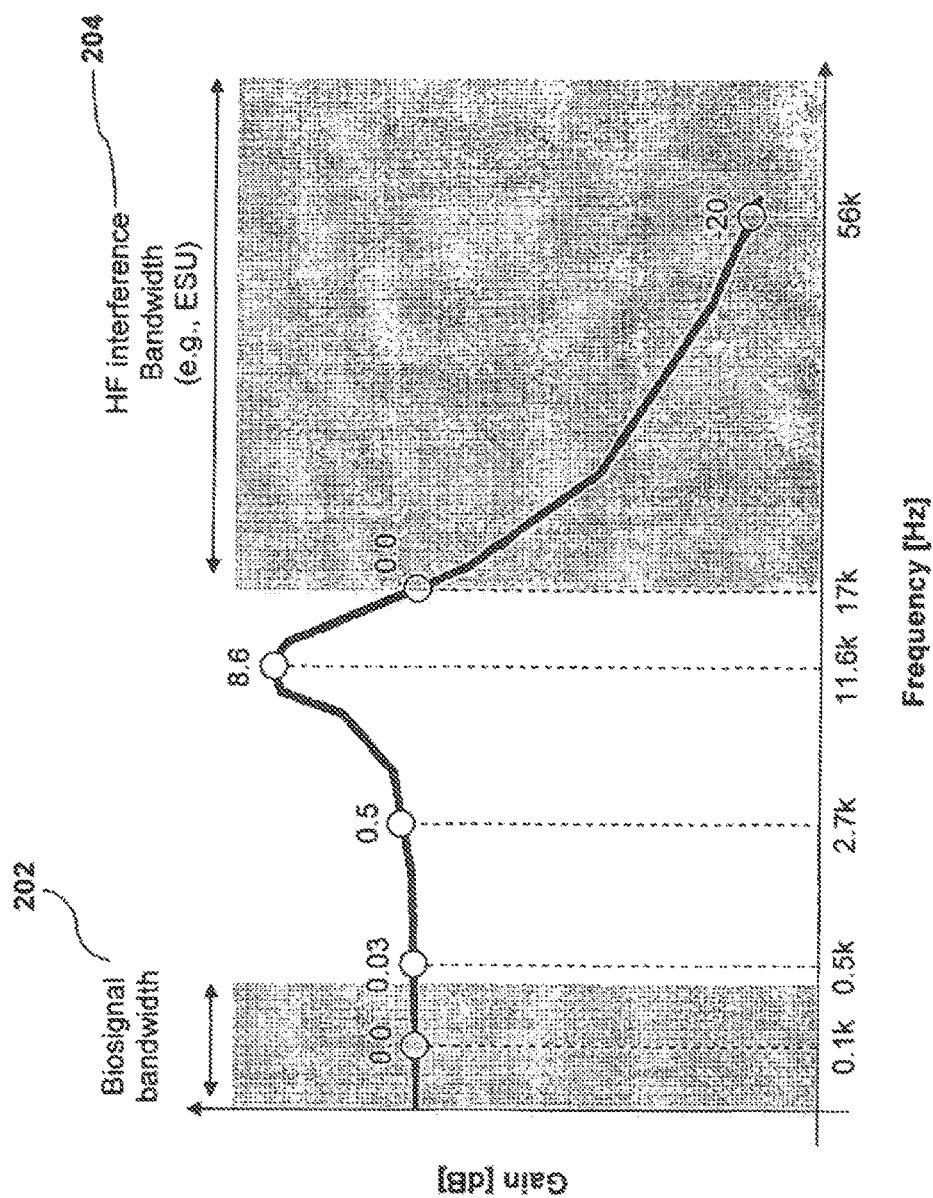
FIG. 6 shows a graph of the active filter frequency response.

FIG. 6 is a graph of the relative gain (dB) versus frequency up to 56 KHz of the active filters. Notice that there is basically no attenuation across the bandwidth of the biosignals 202. While at the same time there is a strong attenuation at frequencies in the HF interference band 204. In the case of the present embodiment, i.e., ESU interference rejection, this is well below the frequencies at which ESUs operate.

HF interferences from ESU devices are usually the result of a lead-to-earth capacitive imbalance between the active and return leads. This imbalance results in the patient being elevated suddenly to a high potential as compared to the earth ground. This potential will generate a small leakage current to the earth, and will perturb any electronic equipment that provides such an earth-ground return path. It is therefore particularly important to design the electronics of the acquisition system such that the capacitive coupling between the patient-side ground and the earth-ground is as small as possible. This is achieved by designing the system such that the capacitive coupling between the patient-side electronics and the computer-side electronics is minimized. This isolation is also needed to guarantee patient's safety, as per IEC 60601-1 requirements.

In one particular embodiment the BAM is supplied with power by the computer means via the DCM and a transformer. The design of this transformer must be optimized to reduce the capacitive coupling between the primary and secondary leads. In another embodiment the patient-side electronics is powered by a battery, preferably a rechargeable battery.

Data between the BAM and DCM are transferred via an optical link, e.g., using opto-couplers, or via magnetic coupling, e.g., using data coils. Data transmission through radio frequency means can also be envisaged.

Immunity to radiated electromagnetic (EM) and radio frequency (RF) interferences are usually handled by the addition of a continuous shield made out of conductive material such as copper or aluminum. This shield can be either a metallic enclosure, or a sprayed conductive paint inside the plastic enclosure housing the electronics. In the present embodiment, both the BAM and DCM electronics are shielded.

The shield of the BAM is electrically connected to the BAM, while the shield of the DCM is connected directly, or via capacitive coupling, to the common of the CDM or the earth ground. As shown in FIG. 4, the two shields are separated by the isolation barrier to guarantee patient isolation to the earth ground (up to 5 kV according to current standards for medical equipment).

Figure 7:
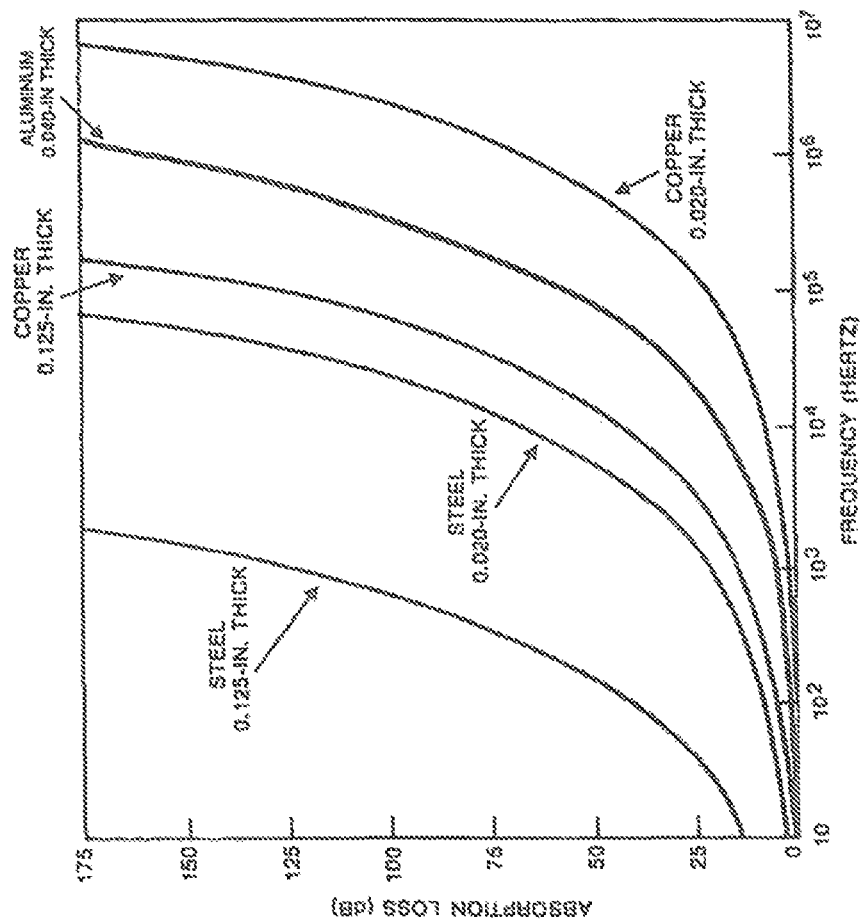
FIG. 7 shows a graph of the skin effect for shield thickness determination

HF interferences originating from, e.g., ESU devices are in the 100 kHz to 1 MHz range, which is much less than EM and RF interferences. Conventional shielding materials therefore may not be sufficient to prevent HF interferences from permeating into the electronics enclosure. Preferably a substantially thicker shield is used. In order to block frequencies from 20 kHz onwards, a minimum aluminum shield depth of 0.020" or more is preferred, see FIG. 7. Of course using thicker shielding or materials with stronger shielding capabilities should yield equal or better results. Yet, the lack of sufficient shielding will limit the achievable performance of the system in the presence of HF interference.

In spite of efforts to obtain interference-free EEG signals from a subject during the presence of ESU or other HF interferences, there will likely always be circumstances where EEG signals are corrupted by ESU or similar interferences. Therefore, it is advantageous for the medical instrument signal processor design to identify exactly when ESU energy, or similar interferences, are present so that appropriate signal processing strategies can be implemented.

Therefore, a preferred embodiment of the present invention incorporates a subsystem, so called Cross-Barrier Voltage Measurement (CBVM), at the isolation barrier interface which reliably senses when ESU energy or similar interferences are induced to the subject, and communicate that occurrence to the main processor. The subsystem's output can be quasi-linear ADC coded or simply processed as a binary flag with a decision threshold set to a level to be a reasonable balance between false-positives and failure to respond to valid occurrences. Additionally, the subsystem output could be used to remove the interference when they occur by a number of methods including the methods explained in *A wavelet based de-noising technique for ocular artifact correction of the electroencephalogram.* Zikov, et al. Eng. in Med. and Bio. $24^{th}$ Ann. Conf. p 98-105 vol. 1 (2002).

Figure 8:
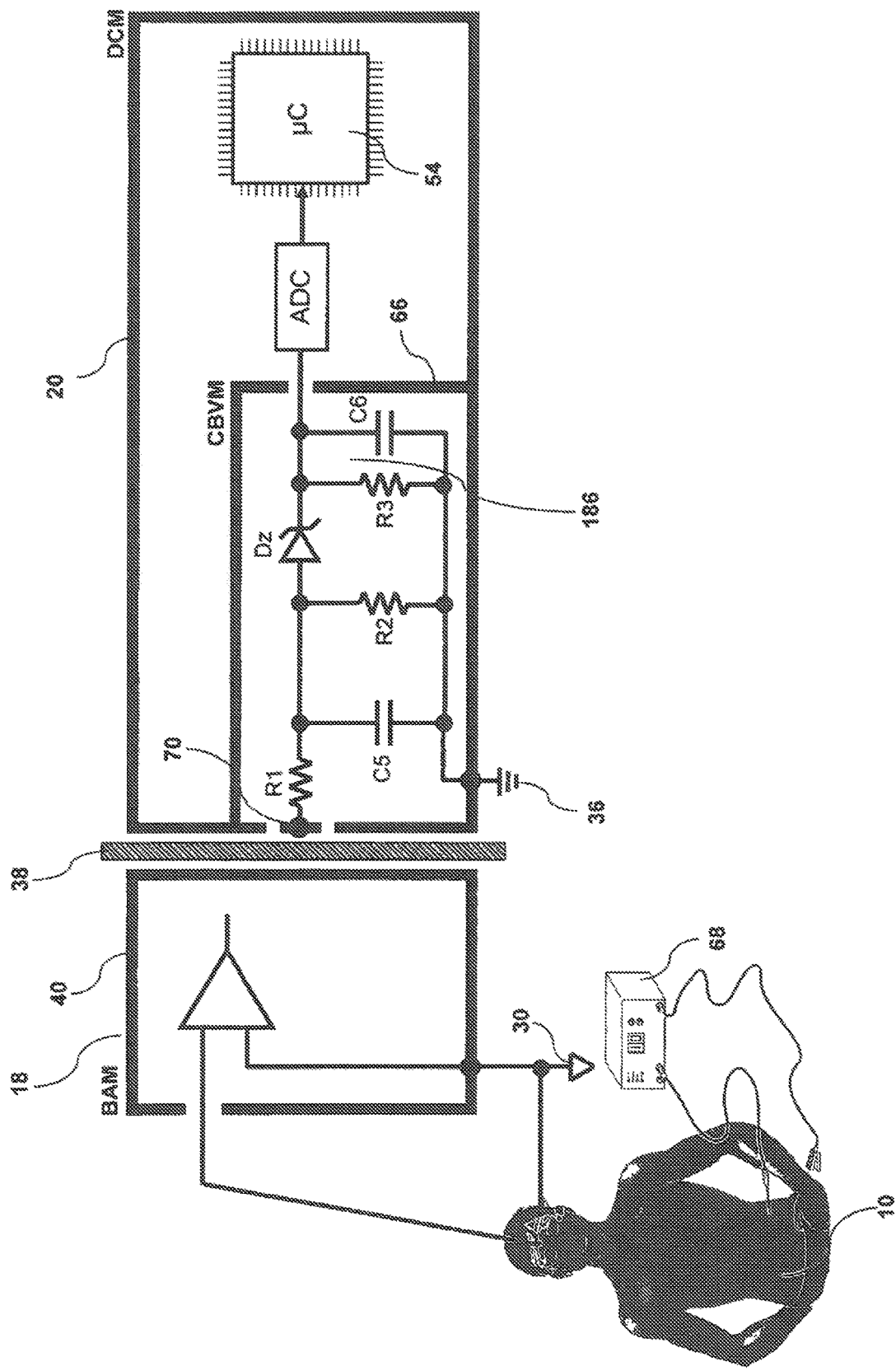
FIG. 8 shows, in diagrammatic form the cross-barrier voltage measurement circuitry.
Figure 9:
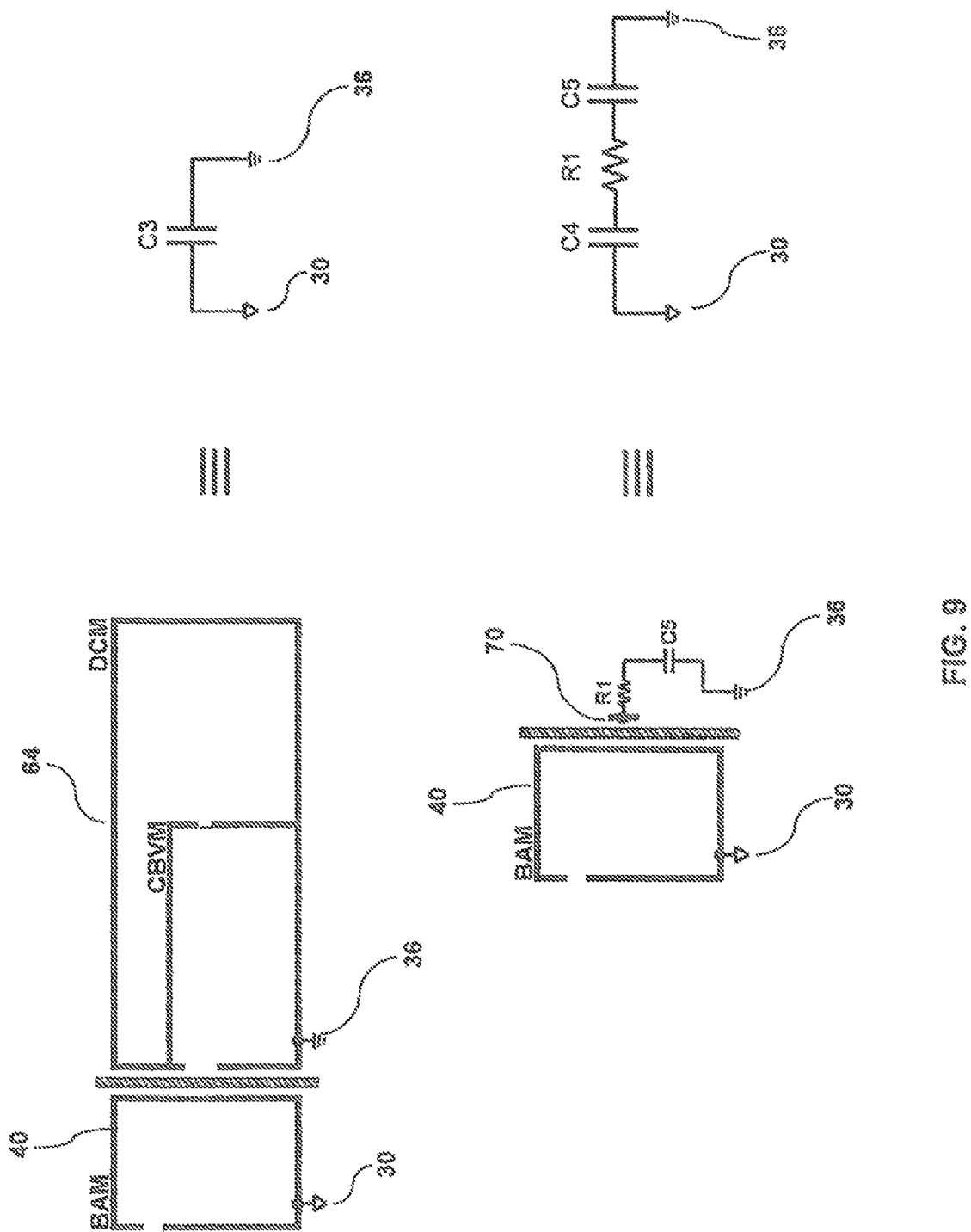
FIG. 9 shows, in diagrammatic form the equivalent electrical circuitries of the shield-isolation barrier-shield interface, and the measurement circuit detector

The CBVM subsystem is illustrated in FIG. 8. The HF interference measure is based on the principle that two conductive plates separated by a dielectric material form a capacitive coupling. Hence, the BAM 18 and DCM 20 shield surfaces that are directly adjacent to the isolation-barrier are creating a capacitive coupling C3 between the patient ground and the earth-ground, as shown in FIG. 9. The CBVM sensing element 70 follows the same principle: a window is opened in the DCM shield 64. In this window, a conductive surface is placed parallel to the BAM shield 40. This surface is kept isolated from the DCM shield 64, and thus is left floating from the earth ground. A capacitive coupling C4 therefore exists between the patient ground and the resistor R1 in series with C5, as shown in FIG. 9. Note that the DCM shield opening creates an opening through the isolation-barrier for EM and RF interferences that can then enter the DCM 20. It is therefore necessary to add a secondary shield around the CBVM circuitry in order to block these interferences from permeating inside the DCM 20 enclosure. The CBVM circuitry includes a signal averaging circuit 186 comprising Dz, R3 and C6 as shown in FIG. 8. The zener diode Dz allows only positive voltage potentials to pass the averaging circuit. The CBVM circuitry also preferably possesses some high-pass filtering characteristics, to better measure and identify the occurrence of HF interference.

Figure 10:
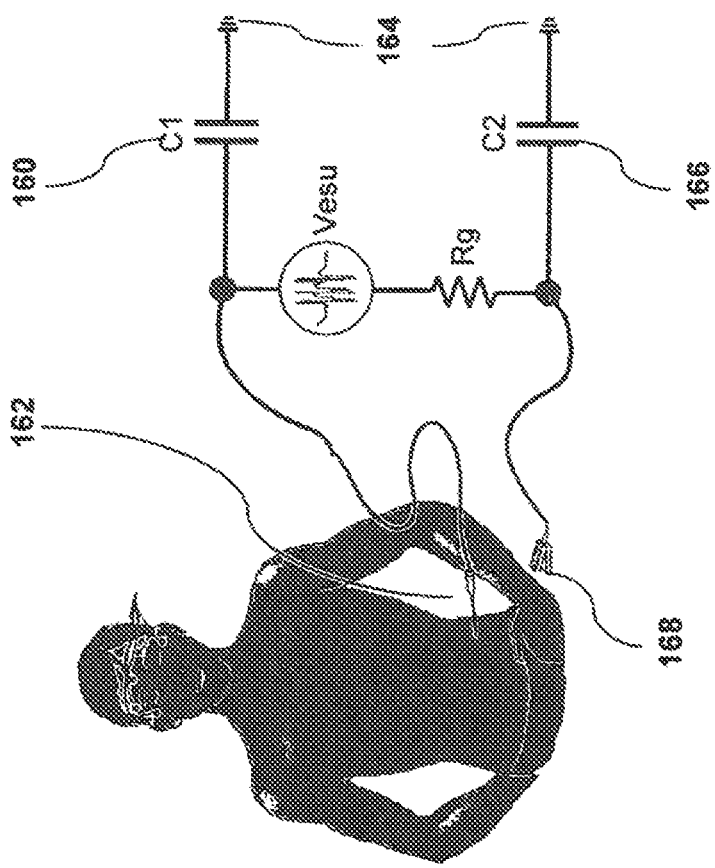
FIG. 10 shows, in diagrammatic form the equivalent electrical circuitry of an Electro-Surgical Unit (ESU)
Figure 10:
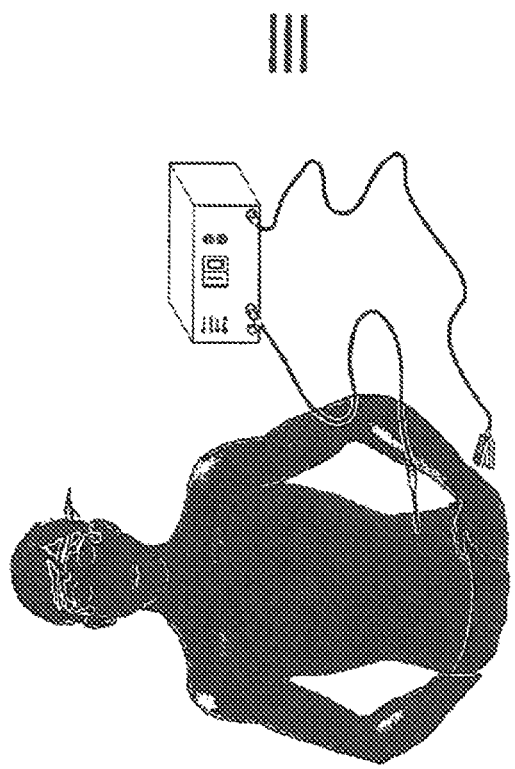

FIG. 10 is a schematic of an ESU generator and patient connections. In most cases, the capacitive coupling C1 160 between the ESU knife 162 and the earth ground 164, and the capacitive coupling C2 166 between the return ESU plate 168 and the earth ground 164 are not equal. This imbalance is responsible for the conducted ESU HF interference.

Figure 11:
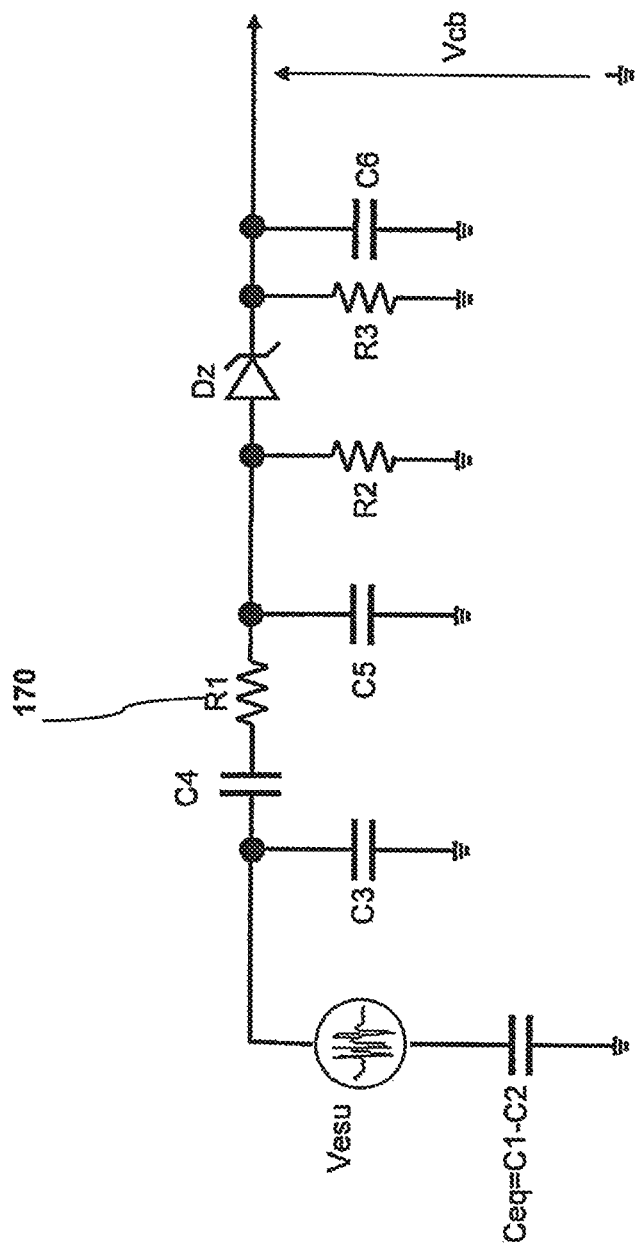
FIG. 11 shows an electrical equivalent of the HF detection circuitry

Based on these principles, the schematic of the system in FIG. 8 can be represented as in FIG. 11. Note that the resistor R1 170 is a low value resistor whose purpose is to limit very fast transient peak currents, e.g., such as electro-static discharges, so that CBVM parts will tend not to be degraded over time and fail.

Figure 12:
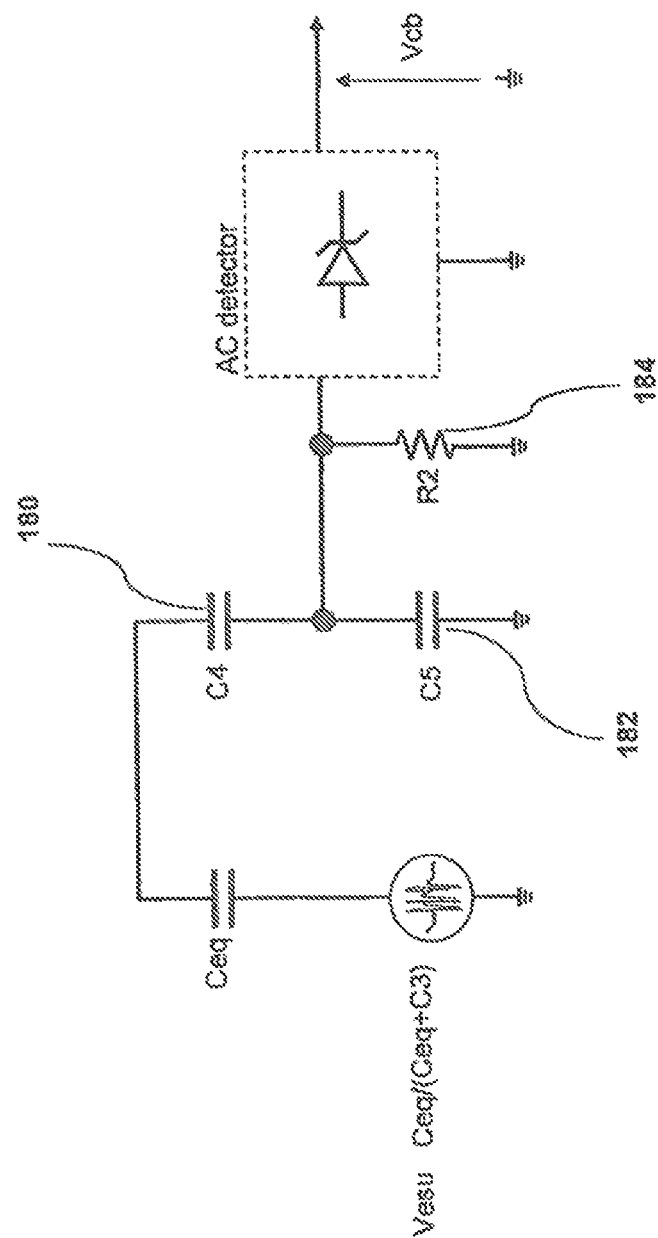
FIG. 12 shows a simplified electrical equivalent of the HF detection circuitry

The circuit in FIG. 11 can thus be further approximated as in FIG. 12. There are two key subcircuits that define the novelty of this measurement system. The first subcircuit is the isolated-interface sampling capacitor, C4 180 and the second subcircuit is the combined high-pass filter and capacitive divider: C4, C5 and R2.

The C5 182 and R2 184 parallel combination form a high-pass filter 186. Note that the high-pass filter 186 can be designed such that it strongly attenuates power-line induced voltages on the patient. Further, the ratio of C4 180 to (C4+C5) defines the reduced AC voltage that is routed to a conventional single phase diode circuit comprising of Dz, R3 and C6. This circuit output is directly representative of the voltage across C5 182.

Figure 13:
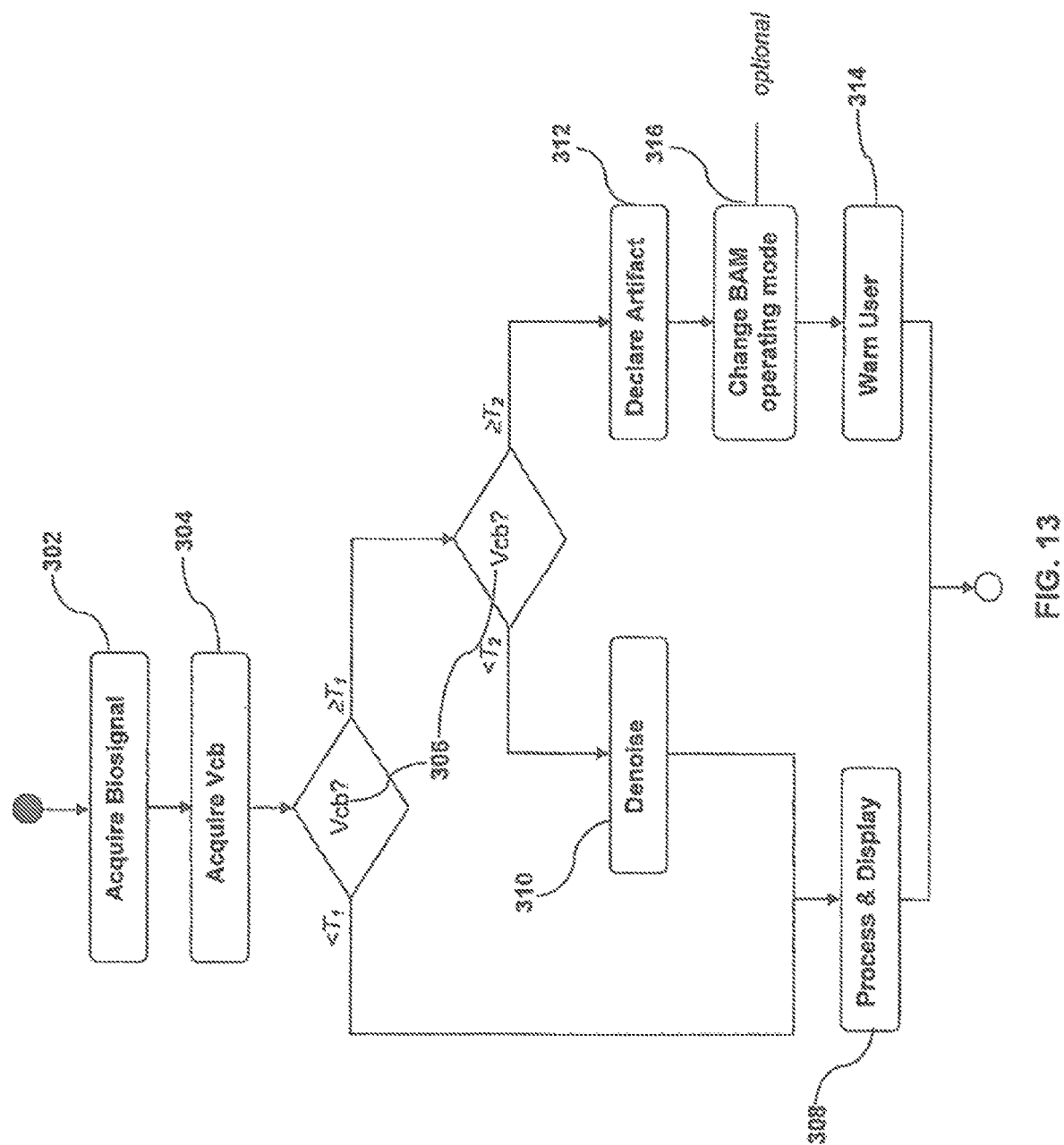
FIG. 13 shows, in diagrammatic form the operation of the software for the invention.

An example of an algorithm for an application where an EEG signal is acquired during surgery is shown in diagrammatic form in FIG. 13. The system acquires both the EEG signals 302 and the Vcb measurement 304. Depending on the Vcb voltage 306, the system will either directly analyze/display 308 the EEG data, or apply a series of filters to further remove some of the perturbing noise 310. If the Vcb voltage 306 is too high, the EEG epoch is rejected from the analysis 312, and a warning message is sent to the user 314. In one embodiment, such occurrence is followed by a command sent to the BAM to change the operating mode of the instrumentation amplifiers 316 in order to provide a prompt recovery once the HF interference disappears. The thresholds T1 and T2 may be made adaptive, depending on the application.

Another useful measure for the detection of corrupting noise in the acquired biosignals is the evolution of Vcb as a function of time. If Vcb changes at rates that fall in the biosignal bandwidth, the HF interferences then act as a carrier for a noise that directly affects the bandwidth of interest. The EEG signal can then be retrieved using adaptive filter and using Vcb time course as a regressor.

In applications which do not have the input active filter for HF rejection, or an adequate low frequency shield, or a low-isolation interface between patient ground and earth ground, the Vcb measure can be used to, e.g., close a series of input relays to prevent the saturation of the instrumentation amplifiers, and reset the post amplification filters. As soon as Vcb returns to a low level, the input relays would open once again and the biosignal would then become immediately available. If no such actions are made during the saturation of the instrumentation amplifiers, it would then take a larger amount of time before recovering the signal of interest once the HF interference disappears.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A method of acquiring signals from a subject in the presence of high frequency (HF) electrical interference comprising the steps of:
    attaching at least 2 electrodes to a subject,
    acquiring signals from the subject using amplification circuitry, with said circuitry comprising:
        at least one input filter for HF electrical interference rejection, and
        an isolation barrier;
    obtaining a quantitative measure of a level of HF electrical interference, and
    transmitting the signals and measured HF electrical interference level to a processor.

2. The method of claim 1 wherein said at least one input filter passes low frequency signals, but filters out those portions of the acquired signals with frequencies above 56 kHz.

3. The method of claim 1 wherein said processor uses the measure of HF electrical interference to modify a behavior of the at least one input filter.

4. The method of claim 1 wherein said method includes the step of delivery of an anesthesia or sedation drug using a closed-loop controller.

5. The method of claim 1 wherein the amplification circuitry comprises two isolated circuits and said quantitative measure of the level of HF electrical interference is measured across a capacitive coupling between the two isolated circuits.

6. The method of claim 1 wherein said signals acquired from said subject are electroencephalograph (EEG) signals.

7. The method of claim 1, wherein the acquired signals are used to determine the depth of anesthesia of the subject.

8. The method of claim 7 wherein both an EEG signal and an EOG signal are acquired.

9. The method of claim 8 wherein the processor uses a wavelet based denoising technique to extract the EEG signal and the EOG signal.

10. An apparatus for acquiring signals from a subject in the presence of high frequency (HF) electrical interference comprising:
    at least 2 electrodes, each acquiring a signal when attached to a subject,
    amplification circuitry for HF electrical interference rejection connected to said at least 2 electrodes for receiving the signals from the at least 2 electrodes, with said circuitry comprising:
        at least one active input filter,
        multistage amplification circuitry,
        an optimized low frequency shield, and
        an isolation barrier where power is transmitted via an optimized transformer, and data is transmitted via at least one data coil;
    wherein said amplification circuitry measures the level of HF electrical interference across said isolation barrier, and
    transmits the acquired signals and measured HF electrical interference level to a processor of the apparatus.

11. The apparatus of claim 10 wherein said at least one active input filter passes low frequency signals, but filters out those portions of the acquired signals with frequencies above 56 kHz.

12. The apparatus of claim 10 wherein said processor uses the measure of HF electrical interference to modify a behavior of the at least one active input filter.

13. The apparatus of claim 10 wherein said apparatus is a component of a closed-loop control anesthesia or sedation drug delivery system.

14. The apparatus of claim 10 wherein the amplification circuitry comprises at least two isolation circuits, and wherein said measuring of the level of HF electrical interference is done through a capacitive coupling between the two isolated circuits.

15. The apparatus of claim 10 wherein said signals acquired from said subject are electroencephalograph (EEG) signals.

16. The apparatus of claim 10 wherein said at least one active input filter is a modified Sallen-Key filter.

17. The apparatus of claim 10 wherein the apparatus is a component of a depth of anesthesia monitoring system.

18. The apparatus of claim 17 wherein the apparatus acquires both an EEG signal and an EOG signal.

19. The apparatus of claim 18 wherein the processor uses a wavelet based denoising technique to extract the EEG signal and the EOG signal.

20. The apparatus of claim 10 wherein the apparatus monitors ECG.

* * * * *